United States Patent
Hosoya et al.

(10) Patent No.: US 8,529,788 B2
(45) Date of Patent: Sep. 10, 2013

(54) PEARLESCENT COMPOSITION

(75) Inventors: Shingo Hosoya, Wakayama (JP);
Yasumitsu Sakuma, Wakayama (JP);
Koji Mine, Wakayama (JP); Takeshi Nakai, Wakayama (JP)

(73) Assignee: Kao Corporation, Tokyo (JP)

( * ) Notice: Subject to any disclaimer, the term of this patent is extended or adjusted under 35 U.S.C. 154(b) by 233 days.

(21) Appl. No.: 12/530,909

(22) PCT Filed: Mar. 11, 2008

(86) PCT No.: PCT/JP2008/054361
§ 371 (c)(1),
(2), (4) Date: Sep. 11, 2009

(87) PCT Pub. No.: WO2008/126558
PCT Pub. Date: Oct. 23, 2008

(65) Prior Publication Data
US 2010/0038585 A1 Feb. 18, 2010

(30) Foreign Application Priority Data

Mar. 12, 2007 (JP) .................................. 2007-062581
Jun. 13, 2007 (JP) .................................. 2007-156791

(51) Int. Cl.
*C09K 3/00* (2006.01)
*C11D 17/00* (2006.01)

(52) U.S. Cl.
USPC ...................................... 252/182.12; 510/416

(58) Field of Classification Search
USPC ...................................... 252/182.12; 510/416
See application file for complete search history.

(56) References Cited

U.S. PATENT DOCUMENTS

| | | | |
|---|---|---|---|
| 4,544,498 A * | 10/1985 | Suzuki | 523/171 |
| 5,019,376 A * | 5/1991 | Uick | 424/70.28 |
| 5,466,395 A * | 11/1995 | Tosaka et al. | 510/416 |
| 5,560,873 A | 10/1996 | Chen et al. | |
| 5,646,106 A | 7/1997 | Chen et al. | |
| 5,925,604 A | 7/1999 | Chen et al. | |
| 6,228,831 B1 * | 5/2001 | Ansmann et al. | 510/416 |
| 6,521,238 B1 * | 2/2003 | Muller et al. | 424/401 |
| RE38,141 E | 6/2003 | Brown | |
| 6,727,217 B1 * | 4/2004 | Nieendick et al. | 510/416 |
| 2004/0180030 A1 | 9/2004 | Maubru | |
| 2006/0079414 A1 | 4/2006 | Nieendick et al. | |

FOREIGN PATENT DOCUMENTS

| | | |
|---|---|---|
| DE | 37 24 547 A1 | 2/1989 |
| DE | 197 54 842 A1 | 6/1999 |
| EP | 332 805 | 9/1989 |
| EP | 1 739 095 | 1/2007 |
| EP | 1 859 780 | 11/2007 |
| EP | 1 862 160 | 12/2007 |
| JP | 60-38310 | 2/1985 |
| JP | 63-267713 A | 11/1988 |
| JP | 6-504781 | 6/1994 |
| JP | 10-510541 | 10/1998 |
| JP | 11-503109 | 3/1999 |
| JP | 2000-178117 | 6/2000 |
| JP | 2000-212031 A | 8/2000 |
| JP | 2003-506393 | 2/2003 |
| JP | 2003-146853 | 5/2003 |
| JP | 2004-196806 | 7/2004 |
| JP | 2005-513071 | 5/2005 |
| JP | 2000-511913 | 9/2009 |
| WO | WO 92/13512 | 8/1992 |
| WO | WO 98/50006 | 11/1998 |
| WO | WO 01/10403 A1 | 2/2001 |

OTHER PUBLICATIONS

Chinese Office Action issued Dec. 21, 2010, in Patent Application No. 200880008028.2 (with English-language translation).
U.S. Appl. No. 13/119,196, filed Mar. 16, 2011, Hosoya, et al.
Office Action issued May 1, 2012, in Japanese Patent Application No. 2008-063020 (with English-language translation).
Office Action issued Apr. 19, 2013, in Japanese Patent Application No. 2008-131941 filed May 20, 2008.
Observations by a third party mailed May 6, 2013 in the corresponding European Patent Application No. 08721777.4, 4 pages.
Supplementary European Search Report issued Jul. 15, 2013, in European Patent Application No. 08721777.4 filed Mar. 11, 2008.

* cited by examiner

Primary Examiner — Peter F Godenschwager
(74) Attorney, Agent, or Firm — Oblon, Spivak, McClelland, Maier & Neustadt, L.L.P.

(57) ABSTRACT

A pearly luster composition containing a fatty acid glycol ester and water, and further containing any one selected from the group consisting of (1) a polyoxyalkylene nonionic surfactant and a fatty acid contained in an amount of from 0.3 to 3% by weight of the pearly luster composition, (2) a polyoxyalkylene nonionic surfactant and an aliphatic alcohol contained in an amount of from 0.3 to 3% by weight of the pearly luster composition, (3) a fatty acid monoglyceride contained in an amount of from 0.3 to 3% by weight of the pearly luster composition, and (4) an aliphatic ether contained in an amount of from 0.3 to 3% by weight of the pearly luster composition, as a crystallization additive. The pearly luster composition of the present invention is suitably used for shampoos, conditioners, body shampoos, liquid detergents, and the like.

18 Claims, 3 Drawing Sheets

PEARLESCENT COMPOSITION

TECHNICAL FIELD

The present invention relates to a pearly luster composition and a method for producing the pearly luster composition. More specifically, the present invention relates to a pearly luster composition, which can be suitably used to enhance the added values of shampoos, conditioners, body shampoos, liquid detergents, and the like, and a method for producing the pearly luster composition.

BACKGROUND ART

Conventionally, in order to enhance the added values of shampoos, conditioners, body shampoos, cosmetics, liquid detergents, and the like, a base material giving a pearly luster has been used. As a main component for giving a pearly luster in the pearly luster composition, fatty acid glycol esters, fatty acid monoalkylolamides, fatty acids, and the like have been known (see Patent Publication 1). Among them, various fatty acid glycol esters have been studied as a main component in the pearly luster composition. However, when the amount of a fatty acid glycol ester formulated is increased to obtain a sufficient pearly luster, a viscosity under room temperature is increased, so that fluidity is lowered. Therefore, a pearly luster composition in which a specified nonionic surfactant is used together has been suggested (see Patent Publication 2).

In addition, other base materials giving a pearly luster have been also studied. For example, Patent Publication 3 discloses a pearly luster concentrate containing an aliphatic compound such as an aliphatic alcohol, a fatty acid monoglyceride, or an aliphatic ether, a surfactant, and a polyol, in place of a fatty acid glycol ester. Patent Publication 4 discloses a pearly luster agent concentrate containing an aliphatic alcohol, a fatty acid monoglyceride, an aliphatic ether, or the like, having a very long chain.
Patent Publication 1: JP-A-Hei-6-504781
Patent Publication 2: JP2000-212031 A
Patent Publication 3: JP2000-511913 A
Patent Publication 4: JP2003-506393 A

SUMMARY OF THE INVENTION

The present invention relates to:
[1] a pearly luster composition containing a fatty acid glycol ester and water, and further containing any one selected from the group consisting of (1) a polyoxyalkylene nonionic surfactant and a fatty acid contained in an amount of from 0.3 to 3% by weight of the pearly luster composition, (2) a polyoxyalkylene nonionic surfactant and an aliphatic alcohol contained in an amount of from 0.3 to 3% by weight of the pearly luster composition, (3) a fatty acid monoglyceride contained in an amount of from 0.3 to 3% by weight of the pearly luster composition, and (4) an aliphatic ether contained in an amount of from 0.3 to 3% by weight of the pearly luster composition, as a crystallization additive; and
[2] a method for producing the pearly luster composition as defined in any one of claims 1 to 8, including the step of cooling a molten mixture solution containing a fatty acid glycol ester, water, and a crystallization additive selected from the group consisting of a fatty acid and a polyoxyalkylene nonionic surfactant, an aliphatic alcohol and a polyoxyalkylene nonionic surfactant, a fatty acid monoglyceride, and an aliphatic ether, to a temperature lower than a melting point of the fatty acid glycol ester.

DETAILED DESCRIPTION OF THE INVENTION

Figure 1:
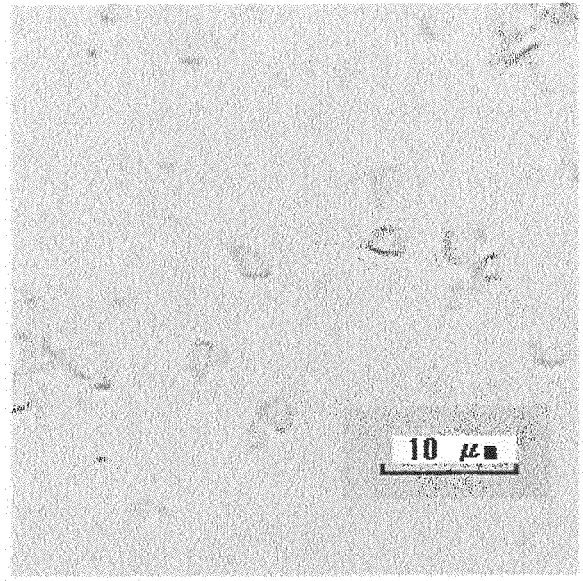
FIG. 1 is a photograph of crystals in the pearly luster composition obtained in Example 2, taken with a color laser microscope.

When the pearly luster composition is formulated in cosmetics, detergents, or the like, it is desired that a sufficient pearly texture is exhibited with the formulation in an amount as small as possible. From the above viewpoint, a pearly luster composition with a high whiteness, in other words, with a high turbidity has been desired.

In other words, the present invention relates to a pearly luster composition with a high turbidity while maintaining a high pearly luster, and a method for producing the pearly luster composition.

The pearly luster composition of the present invention exhibits an excellent effect that a sufficient pearly texture can be exhibited even with the formulation in a small amount since the turbidity is high while maintaining a high pearly luster of the pearly luster composition.

One of the significant features of the pearly luster composition of the present invention resides in that the pearly luster composition contains a fatty acid glycol ester and water, and further contains any one selected from the group consisting of
(1) a polyoxyalkylene nonionic surfactant and a fatty acid in a specified amount,
(2) a polyoxyalkylene nonionic surfactant and an aliphatic alcohol in a specified amount,
(3) a fatty acid monoglyceride contained in a specified amount of the pearly luster composition, and
(4) an aliphatic ether contained in a specified amount of the pearly luster composition,
as a crystallization additive. In a pearly luster composition in which a main component is a fatty acid glycol ester, the above crystallization additive is formulated, whereby a large amount of fine pearly luster-forming particles containing the fatty acid glycol ester which is a pearly luster-forming component, is precipitated, although the reason therefor is unknown, so that a pearly luster composition having a high turbidity is obtained.

The fatty acid is preferably a saturated or unsaturated fatty acid having 8 to 22 carbon atoms, and may be either linear or branched. Fatty acids having 12 to 18 carbon atoms such as lauric acid, myristic acid, palmitic acid, and stearic acid are more preferable, from the viewpoint of making the crystals finer. Those fatty acids may be used alone or in admixture of two or more kinds.

The aliphatic alcohol is preferably a saturated or unsaturated aliphatic alcohol having 8 to 22 carbon atoms, and may be either linear or branched. Aliphatic alcohols having 12 to 22 carbon atoms such as lauryl alcohol, myristyl alcohol, cetyl alcohol, stearyl alcohol, and behenyl alcohol are more preferable, and aliphatic alcohols having 12 to 18 carbon atoms are even more preferable, from the viewpoint of making the crystals finer. These aliphatic alcohols may be used alone or in admixture of two or more kinds.

The fatty acid monoglyceride is preferably a compound which is an ester of glycerol and a fatty acid, represented by the formula (A):

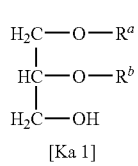

[Ka 1]

wherein either one of $R^a$ and $R^b$ is a hydrogen atom and the other is $-COR^c$, wherein $R^c$ is an alkyl group or alkenyl group having 7 to 21 carbon atoms.

In $R^c$, the number of carbon atoms of the alkyl group and the alkenyl group is preferably from 11 to 17. The alkyl group and the alkenyl group may be either linear or branched.

Suitable examples of the fatty acid monoglyceride in the present invention include lauric acid monoglyceride, myristic acid monoglyceride, palmitic acid monoglyceride, stearic acid monoglyceride, behenic acid monoglyceride, coconut oil fatty acid monoglyceride, palm kernel oil fatty acid monoglyceride, tallow fatty acid monoglyceride, mixtures thereof, and the like. The fatty acid monoglyceride may contain small amounts of diglyceride and triglyceride from the manufacturing process.

The aliphatic ether is preferably a compound represented by the formula (B):

$$R^d\text{—}O\text{—}R^e \tag{B}$$

wherein $R^d$ and $R^e$ are each independently an alkyl group or alkenyl group having 8 to 22 carbon atoms.

In $R^d$ and $R^e$, the number of carbon atoms of the alkyl group and the alkenyl group is preferably from 12 to 18. Also, the alkyl group and the alkenyl group may be either linear or branched. In addition, the aliphatic ether may be either a single ether or a mixed ether, and thus $R^d$ and $R^e$ may be either identical or different with each other.

Suitable examples of the aliphatic ether in the present invention include dilauryl ether, dimyristyl ether, dicetyl ether, distearyl ether, and the like.

In the present invention, the fatty acids, the aliphatic alcohols, the fatty acid monoglycerides and the aliphatic ethers, mentioned above, are also collectively referred to as an aliphatic compound.

The aliphatic compound is contained in an amount of from 0.3 to 3% by weight and preferably from 0.5 to 2% by weight, of the pearly luster composition. When the aliphatic compound is contained in an amount exceeding 3% by weight, deterioration of the luster and lowering of the turbidity are caused. Although not wanting to be limited by theory, this is presumably due to the fact that excessively fine crystals are generated. Also, the above aliphatic compound is contained in an amount of preferably from 1 to 20 parts by weight, more preferably from 1.5 to 20 parts by weight, even more preferably from 1.5 to 15 parts by weight, and even more preferably from 3 to 10 parts by weight, based on 100 parts by weight of the fatty acid glycol ester set forth below.

The polyoxyalkylene nonionic surfactant that is formulated as the crystallization additive together with the fatty acid and the aliphatic alcohol is a substance having a polyoxyalkylene group such as a polyoxyethylene group and a polyoxypropylene group. In the present invention, since the polyoxyalkylene nonionic surfactant is formulated, the viscosity can be lowered, so that not only a high pearly luster is obtained without impairing fluidity, but also an increase in the turbidity is exhibited.

Specific examples of the polyoxyalkylene nonionic surfactant include polyoxyalkylene alkyl ethers, polyoxyalkylene alkylphenyl ethers, polyoxyalkylene glycol fatty acid esters, polyoxyalkylene fatty acid esters, polyoxyalkylene sorbitan fatty acid esters, polyoxyalkylene fatty acid monoalkanolamides, polyoxyalkylene fatty acid dialkanolamides, and the like. Those polyoxyalkylene nonionic surfactants may be used alone or in admixture of two or more kinds. Among them, polyoxyalkylene alkyl ethers represented by the formula (C):

$$R^1\text{—}O\text{—}(R^2O)_p\text{—}H \tag{C}$$

wherein $R^1$ is a linear or branched, saturated or unsaturated hydrocarbon group having 8 to 20 carbon atoms, $R^2$ is an ethylene group or a propylene group, and p is the number of from 1 to 12 and preferably from 1 to 6, which means an average number of moles,
are preferable.

In the formula (C), $R^1$ is preferably an alkyl group having 8 to 20 carbon atoms or an alkenyl group having 8 to 20 carbon atoms. In addition, $R^2$ includes an ethylene group, an n-propylene group, and an iso-propylene group.

The polyoxyalkylene nonionic surfactant has an HLB value of preferably less than 15, and more preferably from 9 to 12.5, from the viewpoint of suppressing an emulsification of the pearly luster composition and controlling the viscosity. Here, the HLB value is an index showing a hydrophilic-lipophilic balance. In the present invention, the HLB value is a value calculated using the equation according to Oda and Teramura, et al.:

$$HLB=(\Sigma Inorganic\ Value/\Sigma Organic\ Value)\times 10$$

The polyoxyalkylene nonionic surfactant is contained in the pearly luster composition in an amount of preferably 0.5% by weight or more from the viewpoint of lowering the viscosity of the pearly luster composition, and preferably 10% by weight or less from the viewpoint of obtaining an excellent pearly luster. From the above viewpoints, the polyoxyalkylene nonionic surfactant is contained in an amount of preferably from 0.5 to 10% by weight, more preferably from 0.5 to 8% by weight, and even more preferably from 1 to 5% by weight, of the pearly luster composition.

The polyoxyalkylene nonionic surfactant may be formulated in the pearly composition together with the fatty acid monoglyceride and the aliphatic ether.

The fatty acid glycol ester includes, for example, compounds represented by the formula (I):

$$Y\text{—}O\text{—}(CH_2CH_2O)_m\text{—}COR^3 \tag{I}$$

wherein $R^3$ is a linear or branched, saturated or unsaturated hydrocarbon group having 13 to 21 carbon atoms, Y is an hydrogen atom or $-COR^3$ ($R^3$ is as defined above), and m is the number of from 1 to 3, which means an average number of moles.

In the formula (I), $R^3$ is preferably an alkyl group and an alkenyl group, having 13 to 21 carbon atoms. Specifically, $R^3$ includes a pentadecyl group, a heptadecyl group, a heneicosyl group, and the like. In addition, the fatty acid glycol ester may be either a monocarboxylate ester wherein Y is a hydrogen atom, or a dicarboxylate ester wherein Y is —COR$^3$, as represented by the formula (I). In the dicarboxylate ester, R$^3$ may be identical or different.

As the fatty acid glycol ester, those having a melting point of 50° C. or higher are preferable, and those being crystalline are preferable. Therefore, as the fatty acid glycol ester, those having a melting point of 50° C. or higher and being crystalline are preferable. Specifically, the fatty acid glycol ester includes monoethylene glycols such as ethylene glycol monopalmitate, ethylene glycol monostearate, ethylene glycol monoisostearate, ethylene glycol dipalmitate, ethylene glycol distearate, and ethylene glycol dibehenate; diethylene glycols thereof; and triethylene glycols thereof; and the like. Those fatty acid glycol esters may be used alone or in admixture of two or more kinds.

Incidentally, when the fatty acid glycol esters are used in admixture of two or more kinds, the fatty acid glycol ester may be a mixture of the fatty acid glycol esters each prepared, and may be a mixture of the fatty acid glycol esters obtained by a reaction using a mixture of fatty acids having different lengths of the alkyl chains and glycol. For example, from the reaction of a mixture of palmitic acid and stearic acid with glycol, a mixture of ethylene glycol dipalmitate, ethylene glycol monopalmitate and monostearate, and ethylene glycol distearate is obtained. In the mixture of fatty acids used upon the reaction of the mixture of different fatty acids with glycol, the percentage of each fatty acid is preferably 85% by weight or less.

In the fatty acid glycol esters exemplified above, as the preferable fatty acid glycol esters in the present invention, ethylene glycol distearate, ethylene glycol dipalmitate, ethylene glycol monostearate, ethylene glycol monopalmitate, and ethylene glycol dibehenate, and a mixture of ethylene glycol dipalmitate, ethylene glycol monopalmitate and monostearate, and ethylene glycol distearate, are preferable.

The fatty acid glycol ester is contained in the pearly luster composition in an amount of preferably 15% by weight or more from the viewpoint of giving the pearly luster, and preferably 30% by weight or less from the viewpoint of fluidity. From the above viewpoints, the fatty acid glycol ester is contained in an amount of preferably from 15 to 30% by weight, more preferably from 15 to 25% by weight, and even more preferably from 18 to 25% by weight, of the pearly luster composition.

The water is contained in an amount of preferably from 25 to 75% by weight, more preferably from 40 to 75% by weight, and even more preferably from 50 to 75% by weight, from the viewpoint of adjustments of the concentration and the viscosity of the pearly luster composition.

Further, the pearly luster composition of the present invention may contain an alkyl sulfate, a fatty acid monoalkylolamide, or the like.

The alkyl sulfate acts as a dispersing agent, and includes, for example, alkyl sulfates which may have a polyoxyalkylene group represented by the formula (II):

$$R^4—O—(R^5O)_n—SO_3M \quad (II)$$

wherein R$^4$ is a linear or branched, saturated or unsaturated hydrocarbon group having 8 to 20 carbon atoms, R$^5$ is an ethylene group or a propylene group, M is an alkali metal, an alkaline-earth metal, an ammonium ion, or a hydroxyalkyl-substituted ammonium having 2 or 3 carbon atoms, and n is the number of from 0 to 8, which means an average number of moles, and the like.

In the formula (II), R$^4$ is preferably an alkyl group and an alkenyl group, having 8 to 20 carbon atoms. Specifically, R$^4$ includes a lauryl group, a myristyl group, a palmityl group, a stearyl group, and the like. R$^5$ includes the same groups as R$^2$ mentioned above. n is preferably from 0 to 4.

Suitable examples of the alkyl sulfate include sodium lauryl sulfate, triethanolamine lauryl sulfate, sodium polyoxyethylene lauryl ether sulfate, and triethanolamine polyoxyethylene lauryl ether sulfate. Those alkyl sulfates may be used alone or in admixture of two or more kinds.

The alkyl sulfate is contained in the pearly luster composition in an amount of preferably 5% by weight or more from the viewpoint of homogenously mixing each component, and preferably 15% by weight or less from the viewpoint of fluidity. From the above viewpoints, the alkyl sulfate is contained in an amount of preferably from 5 to 15% by weight, more preferably from 8 to 15% by weight, and even more preferably from 8 to 13% by weight.

The fatty acid monoalkylolamide is effective in an increase in the luster, and includes, for example, those represented by the formula (III):

$$R^6CO—NH—R^7OH \quad (III)$$

wherein R$^6$ is a linear or branched, saturated or unsaturated hydrocarbon group having 7 to 20 carbon atoms, R$^7$ is an ethylene group or a propylene group.

In the formula (III), R$^6$ is preferably an alkyl group and an alkenyl group, having 7 to 20 carbon atoms. Specifically, R$^6$ includes an undecyl group, a tridecyl group, a heptadecyl group, and the like. Also, R$^7$ includes the same groups as R$^2$ mentioned above.

The fatty acid monoalkylolamide includes lauric acid monoethanolamide, lauric acid monopropanolamide, lauric acid monoisopropanolamide, myristic acid monoethanolamide, palmitic acid monoethanolamide, stearic acid monoethanolamide, oleic acid monoethanolamide, oleic acid monoisopropanolamide, coconut oil fatty acid monoethanolamide, coconut oil fatty acid monopropanolamide, coconut oil fatty acid monoisopropanolamide, palm vegetable oil fatty acid monoethanolamide, and the like. Those fatty acid monoalkylolamides can be used alone or in admixture of two or more kinds. Among them, coconut oil fatty acid monoethanolamide, lauric acid monoethanolamide, palmitic acid monoethanolamide, and stearic acid monoethanolamide, are preferable.

The fatty acid monoalkylolamide is contained in the pearly luster composition in an amount of preferably 3% by weight or more from the viewpoint of giving a luster, and preferably 15% by weight or less from the viewpoint of suppressing an increase in the viscosity of the pearly luster composition and increasing fluidity. From the above viewpoints, the fatty acid monoalkylolamide is contained in an amount of preferably from 3 to 15% by weight, more preferably from 3 to 10% by weight, and even more preferably from 5 to 10% by weight, of the pearly luster composition.

Further, in the pearly luster composition of the present invention, a pH adjusting agent, a preservative, salts, alcohols, polyols or the like, may be properly formulated.

The method for producing the pearly luster composition of the present invention is not particularly limited as long as the process includes the step of crystallizing the pearly luster-forming particles containing a fatty acid glycol ester from a molten mixture solution of the raw materials such as a fatty acid glycol ester, a crystallization additive, and water. The specific process includes, for example, a process including the steps of heating the mixture of the raw materials such as a fatty acid glycol ester, a crystallization additive, and water, and thereafter cooling the heated mixture; a process including the steps of mixing a mixture containing water, and a polyoxyalkylene nonionic surfactant, an alkyl sulfate, a fatty acid monoalkylolamide, and the like, as required, with a fatty acid glycol ester and an aliphatic compound in a molten state, and thereafter cooling the mixture, and the like.

In addition, the fatty acid glycol ester and the aliphatic compound may be added thereto as a mixture solution of both compounds each heated to melt or may be separately added thereto. It is preferable that the molten mixture solution of both compounds is added thereto.

The temperature of the molten mixture solution of the raw materials is preferably a temperature not less than the melting point of either the fatty acid glycol ester or the aliphatic compound having a higher melting point and preferably a temperature not more than the boiling point of the mixture. In addition, the temperature of the molten mixture solution of the raw materials is a temperature higher than the melting point of either the fatty acid glycol ester or the aliphatic compound having a higher melting point, more preferably by from 1° to 30° C., and even more preferably by from 1° to 20° C.

The cooling temperature is preferably less than the melting point of the fatty acid glycol ester, more preferably not more than the melting point by 10° C., and even more preferably not more than the melting point by 20° C., from the viewpoint of sufficiently crystallizing the fatty acid glycol ester and the aliphatic compound. Furthermore, the cooling temperature is not more than the melting point of either the fatty acid glycol ester or the aliphatic compound having a lower melting point, preferably by 10° C., and more preferably by 20° C.

In addition, the cooling is preferably a slow cooling with a narrow temperature distribution from the viewpoint of obtaining pearly luster-forming particles having homogenous shapes. From the above viewpoint, the cooling rate is preferably from 0.1° to 10° C./min, more preferably from 0.1° to 5° C./min, and even more preferably from 0.1° to 3° C./min.

After the pearly luster-forming particles are crystallized, it is preferable that the pearly luster-forming particles are further cooled to stabilize the crystals. It is desired that the solution is cooled until a temperature of the solution is from 10° to 40° C., and preferably from 15° to 35° C.

The raw materials are molten and cooled preferably while stirring so that the solution is not separated.

It is desired that the pearly luster composition of the present invention has a viscosity at 30° C. of from 1,000 to 50,000 mPa·s, and preferably from 1,000 to 30,000 mPa·s. In addition, the pearly luster-forming particles have a number-average diameter of the major diameter (number-average major diameter) of preferably from 1 to 6 μm and more preferably from 2 to 5 μm, from the viewpoint of the pearly luster.

EXAMPLES

The following examples further describe and demonstrate embodiments of the present invention. The examples are given solely for the purposes of illustration and are not to be construed as limitations of the present invention.

The properties of the pearly luster compositions obtained in each of Examples and each of Comparative Examples, were determined according to the following methods.

<Number-Average Major Diameter of Pearly Luster-Forming Particles>

The pearly luster composition is diluted 1,000-folds (weight ratio) with water, and the dilution is dropped on a slide glass and allowed to dry naturally, and observed with a color laser microscope (manufactured by KEYENCE CORPORATION). The major diameters of the pearly luster-forming particles confirmed as crystals are randomly determined at one-hundred points. The average value obtained therefrom is defined as the number-average major diameter of the crystals.

<Pearly Luster of Pearly Luster Composition>

The pearly luster composition is diluted 20-folds (weight ratio) with water, and an appearance of the pearly luster is observed with the naked eye, and evaluated according to the following criteria. Incidentally, a composition in which bubbles are commingled is centrifuged to remove bubbles.

<Evaluation Criteria>
1: No luster is found.
2: A low luster is found.
3: A high luster is found.

<Turbidity of Pearly Luster Composition>

The pearly luster composition is diluted 1,000-folds (weight ratio) with water, and the absorbance at a wavelength of 550 nm is determined using a cell having a width of 1 cm with a UV-visible spectrophotometer (UVmini-1240, manufactured by Shimadzu Corporation).

<Viscosity of Pearly Luster Composition>

The pearly luster composition is maintained at 30° C., and the viscosity is determined with a B-type viscometer.

<Melting Point of Fatty Acid Glycol Ester or Aliphatic Compound>

The fatty acid glycol ester or the aliphatic compound is heated so as to raise the temperature at a rate of 5° C./min using a differential scanning calorimeter (Thermo plus DSC8230, manufactured by Rigaku Corporation), and the top of the resulting melting peak is defined as a melting point.

Examples 1 to 6 and Comparative Examples 1 to 3

Figure 2:
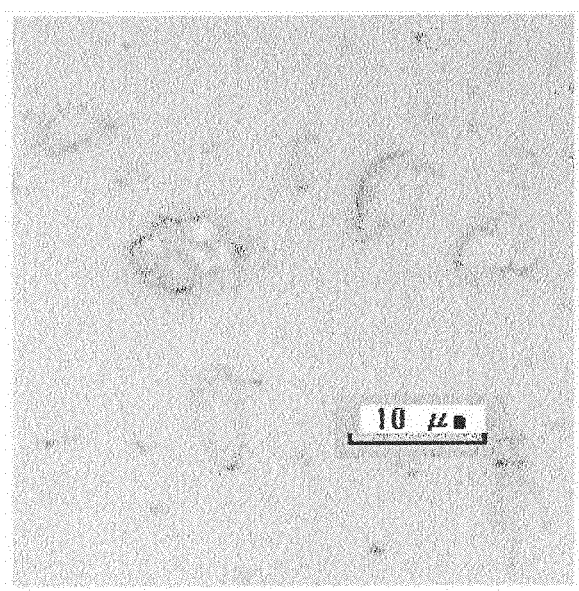
FIG. 2 is a photograph of crystals in the pearly luster composition obtained in Comparative Example 1, taken with a color laser microscope.
Figure 3:
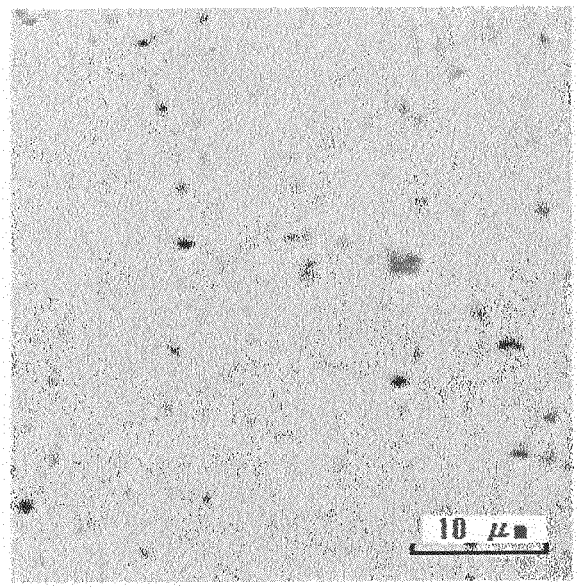
FIG. 3 is a photograph of crystals in the pearly luster composition obtained in Comparative Example 3, taken with a color laser microscope.

A mixture of a fatty acid monoalkylolamide, an alkyl sulfate, a polyoxyalkylene nonionic surfactant, and other components, shown in Table 1 is mixed at 80° C. A fatty acid glycol ester and a fatty acid previously molten and mixed are added thereto in a molten state and mixed. Thereafter, the mixture was cooled at a cooling rate of 0.5° C./min to 20° C., to give a pearly luster composition. Photographs of crystals in the pearly luster compositions (pearly luster-forming particles) obtained in Example 2 and Comparative Examples 1 and 3, taken with a color laser microscope are shown in FIGS. 1 to 3.

TABLE 1

|  | Examples | | | | | | Comparative Examples | | |
| --- | --- | --- | --- | --- | --- | --- | --- | --- | --- |
|  | 1 | 2 | 3 | 4 | 5 | 6 | 1 | 2 | 3 |
| (A) Fatty Acid Glycol Ester: | | | | | | | | | |
| Di-Fatty Acid Ethylene Glycol (C16/C18 = 50/50[1]) | 19.5 | 18.8 | 18.5 | 18.3 | — | 18.8 | 20.0 | 18.8 | 16.0 |
| Di-Fatty Acid Ethylene Glycol (C16/C18 = 20/80[2]) | — | — | — | — | 18.8 | — | — | — | — |
| (B) Fatty Acid: | | | | | | | | | |

TABLE 1-continued

|  | Examples | | | | | | Comparative Examples | | |
|---|---|---|---|---|---|---|---|---|---|
|  | 1 | 2 | 3 | 4 | 5 | 6 | 1 | 2 | 3 |
| Fatty Acid (C14/C16/C18 = 5/30/65[3)]) | 0.5 | 1.2 | 1.5 | — | 1.2 | 1.2 | — | 1.2 | 4.0 |
| Fatty Acid (C16/C18/C20 = 2/97/1[4)]) | — | — | — | 1.7 | — | — | — | — | — |
| (C) Fatty Acid Monoalkylolamide: | | | | | | | | | |
| Coconut Oil Monoethanolamide | 7.5 | 7.5 | 7.5 | 7.5 | 7.5 | 7.5 | 7.5 | 7.5 | 7.5 |
| (D) Alkyl Sulfate: | | | | | | | | | |
| Sodium Polyoxyethylene (2) Lauryl Ether Sulfate[5)] | 10.8 | 10.8 | 10.8 | 10.8 | 10.8 | 10.8 | 10.8 | 10.8 | 10.8 |
| (E) Polyoxyalkylene Nonionic Surfactant: | | | | | | | | | |
| Polyoxyethylene (4) Lauryl Ether[5)] [HLB: 9.7] | 4.0 | 4.0 | 4.0 | 4.0 | 4.0 | — | 4.0 | — | 4.0 |
| Polyoxyethylene (6) Lauryl Ether[5)] [HLB: 12.1] | — | — | — | — | — | 4.0 | — | — | — |
| (F) Other Component: | | | | | | | | | |
| 50% Aqueous Citric Acid Solution | 0.165 | 0.165 | 0.165 | 0.165 | 0.165 | 0.165 | 0.165 | 0.165 | 0.165 |
| Sodium Benzoate | 0.7 | 0.7 | 0.7 | 0.7 | 0.7 | 0.7 | 0.7 | 0.7 | 0.7 |
| Water | Balance | Balance | Balance | Balance | Balance | Balance | Balance | Balance | Balance |
| Content of (B) (Parts by Weight) Based on 100 Parts by Weight of (A) | 2.6 | 6.4 | 8.1 | 9.3 | 6.4 | 6.4 | — | 6.4 | 25 |
| Number-Average Major Diameter of Pearly Luster-Forming Particles (μm) | 3.94 | 3.89 | 3.38 | 2.99 | 3.67 | 4.87 | 6.52 | 3.50 | 0.99 |
| Pearly Luster | 3 | 3 | 3 | 3 | 3 | 3 | 3 | 2 | 1 |
| Turbidity | 0.89 | 0.95 | 0.95 | 0.89 | 0.94 | 1.00 | 0.67 | 0.83 | 0.49 |
| Viscosity (mPa · s) | — | 17,000 | — | — | — | — | 5,850 | 98,000 | — |

Notes)
The compositional ratio is expressed in % by weight.
[1)]An ester of a mixture of palmitic acid (C16)/stearic acid (C18) = 50/50 (weight ratio) and ethylene glycol, melting point: 61.8° C.
[2)]An ester of a mixture of palmitic acid (C16)/stearic acid (C18) = 20/80 (weight ratio) and ethylene glycol, melting point: 72.4° C.
[3)]A mixture of myristic acid (C14)/palmitic acid (C16)/stearic acid (C18) = 5:30:65 (weight ratio), melting point: 59.7° C.
[4)]A mixture of palmitic acid (C16)/stearic acid (C18)/arachidic acid (C20) = 2:97:1 (weight ratio), melting point: 73.0° C.
[5)]The number in parentheses shows the number of moles of ethylene oxide.

It can be seen from the above results that the pearly luster compositions of Examples 1 to 6 have a high pearly luster and a high turbidity. On the other hand, it can be seen that the pearly luster composition of Comparative Example 1 in which a fatty acid is not formulated has a high pearly luster, but contains large pearly luster-forming particles and has a low turbidity. In addition, it can be seen that the pearly luster composition of Comparative Example 2 in which a polyoxyalkylene nonionic surfactant is not formulated has a markedly high viscosity, is poor in fluidity, and has a low pearly luster as compared to the pearly luster compositions of Examples, and that the pearly luster composition of Comparative Example 3 in which a fatty acid is formulated in an given amount or more has a lower pearly luster and also a markedly low turbidity.

Examples 7 to 15 and Comparative Examples 4 to 7

Figure 4:
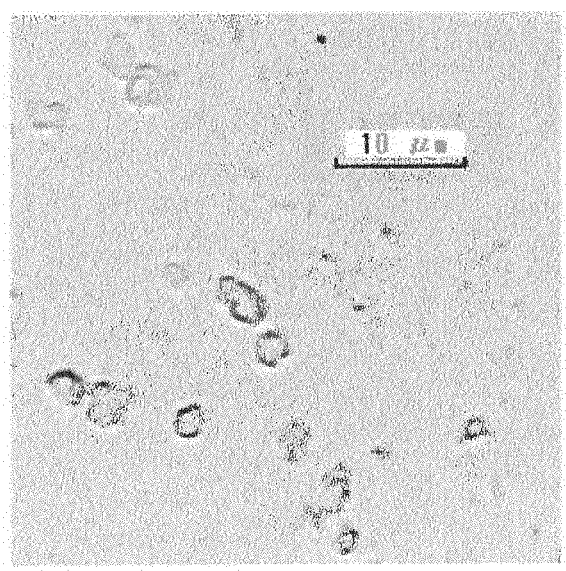
FIG. 4 is a photograph of crystals in the pearly luster composition obtained in Example 9, taken with a color laser microscope.
Figure 5:
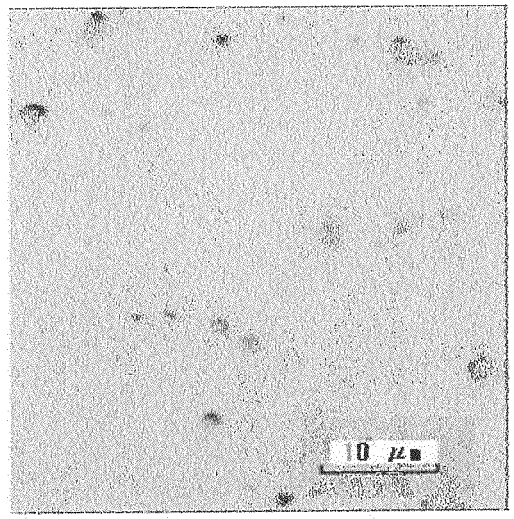
FIG. 5 is a photograph of crystals in the pearly luster composition obtained in Comparative Example 6, taken with a color laser microscope.

A mixture of a fatty acid monoalkylolamide, an alkyl sulfate, a polyoxyalkylene nonionic surfactant, and other components, shown in Table 2 was mixed at 80° C. A fatty acid glycol ester and an aliphatic alcohol, a fatty acid monoglyceride, or an aliphatic ether, shown in Table 2, previously molten and mixed were added thereto in a molten state and mixed. Thereafter, the mixture was cooled at a cooling rate of 0.5° C./min to 20° C., to give a pearly luster composition. Photographs of crystals in the pearly luster compositions (pearly luster-forming particles) obtained in Example 9 and Comparative Example 6, taken with a color laser microscope are shown in FIGS. 4 and 5.

TABLE 2

| | Examples | | | | | | | | | Comparative Examples | | | |
|---|---|---|---|---|---|---|---|---|---|---|---|---|---|
| | 7 | 8 | 9 | 10 | 11 | 12 | 13 | 14 | 15 | 4 | 5 | 6 | 7 |
| (A) Fatty Acid Glycol Ester: | | | | | | | | | | | | | |
| Di-Fatty Acid Ethylene Glycol (C16/C18 = 50/50[1)] | 18.8 | 18.8 | — | — | 18.8 | 17.9 | 18.8 | 18.8 | 18.8 | 16.0 | — | 16.0 | 16.0 |
| Di-Fatty Acid Ethylene Glycol (C16/C18 = 20/80[2)] | — | — | 18.5 | 17.0 | — | — | — | — | — | — | 16.0 | — | — |
| (B) Aliphatic Alcohol: | | | | | | | | | | | | | |
| Cetyl Alcohol[3)] | 1.2 | — | — | — | — | — | — | — | — | — | — | — | — |
| Stearyl Alcohol[4)] | — | 1.2 | 1.5 | — | — | — | — | — | 0.4 | 4.0 | — | — | — |
| Behenyl Alcohol[5)] | — | — | — | 3.0 | — | — | — | — | — | — | 4.0 | — | — |
| (C) Fatty Acid Monoglyceride: | | | | | | | | | | | | | |
| Fatty Acid Monoglyceride (C16/C18 = 25/75[6)]) | — | — | — | — | 1.2 | 2.1 | — | — | 0.4 | — | — | 4.0 | — |
| Fatty Acid Monoglyceride (C18/C18F1/C18F2/Others = 5/65/15/15)[7)] | — | — | — | — | — | 1.2 | — | — | — | — | — | — | — |
| (D) Aliphatic Ether: | | | | | | | | | | | | | |
| Distearyl Ether[8)] | — | — | — | — | — | — | — | 1.2 | 0.4 | — | — | — | 4.0 |
| (E) Fatty Acid Monoalkylolamide: | | | | | | | | | | | | | |
| Coconut Oil Fatty Acid Monoethanolamide | 7.5 | 7.5 | 7.5 | 7.5 | 7.5 | 7.5 | 7.5 | 7.5 | 7.5 | 7.5 | 7.5 | 7.5 | 7.5 |
| (F) Alkyl Sulfate: | | | | | | | | | | | | | |
| Sodium Polyoxyethylene (2) Lauryl Ether Sulfate | 10.8 | 10.8 | 10.8 | 10.8 | 10.8 | 10.8 | 10.8 | 10.8 | 10.8 | 10.8 | 10.8 | 10.8 | 10.8 |
| (G) Polyoxyalkylene Nonionic Surfactant: | | | | | | | | | | | | | |
| Polyoxyethylene (4) Lauryl Ether[9)] [HLB: 9.7] | 4.0 | 4.0 | 4.0 | 4.0 | 4.0 | 4.0 | 4.0 | 4.0 | 4.0 | 4.0 | 4.0 | 4.0 | 4.0 |
| (H) Other Component: | | | | | | | | | | | | | |
| 50% Aqueous Citric Acid Solution | 0.165 | 0.165 | 0.165 | 0.165 | 0.165 | 0.165 | 0.165 | 0.165 | 0.165 | 0.165 | 0.165 | 0.165 | 0.165 |
| Sodium Benzoate | 0.7 | 0.7 | 0.7 | 0.7 | 0.7 | 0.7 | 0.7 | 0.7 | 0.7 | 0.7 | 0.7 | 0.7 | 0.7 |
| Water | Balance | Balance | Balance | Balance | Balance | Balance | Balance | Balance | Balance | Balance | Balance | Balance | Balance |
| Content of (B) + (C) + (D) (Parts by Weight) Based on 100 Parts by Weight of (A) | 6.4 | 6.4 | 8.1 | 17.6 | 6.4 | 11.7 | 6.4 | 6.4 | 6.4 | 25.0 | 25.0 | 25.0 | 25.0 |
| Number-Average Major Diameter of Pearly Luster-Forming Particles (μm) | 3.04 | 3.68 | 2.86 | 4.36 | 4.90 | 3.43 | 3.45 | 3.49 | 3.66 | 1.09 | 1.99 | 1.49 | 6.15 |
| Pearly Luster | 3 | 3 | 3 | 2 | 3 | 3 | 3 | 3 | 3 | 1 | 2 | 1 | 1 |
| Turbidity | 0.89 | 0.92 | 0.97 | 1.03 | 1.11 | 0.87 | 0.97 | 1.03 | 0.97 | 0.46 | 0.61 | 0.88 | 0.89 |

Notes)
The compositional ratio is expressed in % by weight.
[1)]An ester of a mixture of palmitic acid (C16)/stearic acid (C18) = 50/50 (weight ratio) and ethylene glycol, melting point: 61.8° C.
[2)]An ester of a mixture of palmitic acid (C16)/stearic acid (C18) = 20/80 (weight ratio) and ethylene glycol, melting point: 72.4° C.
[3)]melting point: 52.8° C., containing other higher alcohol in an amount of 2% by wt.
[4)]melting point: 62.0° C., containing other higher alcohol in an amount of 2% by wt.
[5)]melting point: 71.4° C., containing an aralkyl alcohol in an amount of 10% by weight and other higher alcohol in an amount of 2% by weight
[6)]A mixture of myristic acid monoglyceride (C16)/stearic acid monoglyceride (C18) = 25/75 (weight ratio), melting point: 72.3° C.
[7)]A mixture of a fatty acid monoglyceride having 18 carbon atoms and other fatty acid monoglyceride (mixing ratio is weight ratio) F1 shows that the fatty acid monoglyceride has one unsaturated bond, and F2 shows that the fatty acid monoglyceride has two unsaturated bonds.
[8)]melting point: 64.0° C., containing other aliphatic ether in an amount of 2% by weight
[9)]The number in parentheses shows the number of moles of ethylene oxide.

It can be seen from the above results that, among Examples, the pearly luster compositions of Examples 7 to 9 and Examples 11 to 15 have an especially high pearly luster and also a high turbidity. On the other hand, it can be seen that the pearly luster compositions of Comparative Examples 4 to 6 in which an aliphatic alcohol or a fatty acid monoglyceride is formulated in a given amount or more lack a luster as the pearly luster compositions, and that the pearly luster composition of Comparative Example 7 in which an aliphatic ether is formulated in a given amount or more also lacks a pearly luster. Particularly, although a difference in amounts of aliphatic alcohols formulated in Example 10 and Comparative Example 5 is small, the results thereof are completely different. It can be seen that Comparative Example 5 in which an aliphatic alcohol is formulated in a given amount or more has a lower turbidity as compared to Example 10.

The pearly luster composition of the present invention is suitably used for shampoos, conditioners, body shampoos, liquid detergents, and the like.

The invention claimed is:

1. A pearly luster composition comprising:
   i) at least one fatty acid glycol ester represented by the formula (I):

Y—O—(CH$_2$CH$^2$O)$_m$—COR$^3$      (I)

wherein R$^3$ is a pentadecyl group or a heptadecyl group, Y is —COR$^3$ (R$^3$ is as defined above), and m is 1, meaning an average number of moles added,
   wherein the fatty acid glycol ester is contained in an amount of from 15 to 30% by weight of the pearly luster composition,
   ii) a polyoxyalkylene alkyl ether nonionic surfactant represented by the formula (C):

R$^1$—O—(R$^2$O)$_p$—H      (C)

wherein R$^1$ is a linear or branched, saturated or unsaturated hydrocarbon group having 8 to 20 carbon atoms, R$^2$ is an ethylene group or a propylene group, and p is the number of from 1 to 12, meaning an average number of moles added, and
   iii) water,
   the pearly luster composition further comprising an aliphatic compound (B) of any one selected from the group consisting of:
   1) a saturated or unsaturated fatty acid having 14 to 18 carbon atoms,
   2) C$_{16-18}$ aliphatic alcohol,
   3) a fatty acid monoglyceride represented by the formula (A):

wherein either one of R$^a$ and R$^b$ is a hydrogen atom and the other is —COR$^c$,
   wherein R$^c$ is an alkyl group or alkenyl group having 15 to 17 carbon atoms, and
   4) a distearyl ether,
   wherein the aliphatic compound as a crystallization additive is contained in an amount of from 0.3 to 3% by weight of the pearly luster compositions and is contained in an amount of from 1.5 to 15 parts by weight based on 100 parts by weight of the fatty acid glycol ester.

2. The pearly luster composition according to claim 1, wherein the crystallization additive is a saturated or unsaturated fatty acid having 14 to 18 carbon atoms, and is contained in an amount of from 1.5 to 10 parts by weight based on 100 parts by weight of the fatty acid glycol ester.

3. The pearly luster composition according to claim 1, wherein the crystallization additive is a C$_{16-18}$ aliphatic alcohol, and is contained in an amount of from 1.5 to 10 parts by weight based on 100 parts by weight of the fatty acid glycol ester.

4. The pearly luster composition according to claim 3, further comprising an alkyl sulfate.

5. the pearly luster composition according to claim 1, wherein the crystallization additive is a fatty acid monoglyceride represented by the formula (A), and is contained in an amount of from 1.5 to 11.7 parts by weight based on 100 parts by weight of the fatty acid glycol ester.

6. The pearly luster composition according, to claim 5, further comprising an alkyl sulfate.

7. The pearly luster composition according to claim 1, further comprising a fatty acid monoalkylolamide represented by the formula (III):

R$^6$CO—NH—R$^7$OH      (III)

wherein R$^6$ is a linear or branched, saturated or unsaturated hydrocarbon group having 7 to 20 carbon atoms, R$^7$ is an ethylene group or a propylene group,
wherein the fatty acid monoalkvlolamide is contained in an amount of from 3 to 10% by weight of the pearly luster composition.

8. The pearly luster composition according to claim 1, which is in the form of pearly luster-forming particles having a number-average major diameter of from 1 to 6 μm.

9. The pearly luster composition according to claim 8, wherein the number-average major diameter is from 2 to 5 μm.

10. A method for producing the pearly luster composition as defined claim 1, comprising cooling a molten mixture solution comprising components (i), (ii), (iii) and the aliphatic compound, to a temperature lower than a melting point of the fatty acid glycol ester.

11. The pearly luster composition according to claim 1, wherein each of the fatty acid, C$_{16-18}$ aliphatic alcohol, the fatty acid monoglyceride, or the distearyl ether, when present, is contained in an mount of from 0.5 to 2% by weight of the pearly luster composition.

12. The pearly luster composition according to claim 1, wherein the fatty acid glycol ester is present in an amount of from 18 to 25% by weight.

13. The pearly luster composition according to claim 1, wherein the water is present in an amount of from 50 to 75% by weight.

14. The pearly luster composition according to claim 1, which has a viscosity at 30° C. of from 1,000 to 50,000 MPa·s.

15. The pearly luster composition according to claim 1, wherein the crystallization additive is a distearyl ether, wherein the distearly ether is contained in an amount of from 1.5 to 10 parts by weight based on 100 parts by weight of the fatty acid glycol ester.

16. The pearly luster composition according to claim 1, wherein. the fatty acid glycol ester is a mixture of two or more fatty acid glycol esters obtained by a reaction using a mixture of fatty acids having different lengths of the alkyl chains and glycol, and wherein the percentage of each fatty acid used on the reaction is 85% by weight or less of the mixture of different fatty acids.

17. The pearly luster composition according to claim 1, further comprising a fatty acid monoalkylolamide represented by the formula (III) and an alkyl sulfate represented by the formula (II):

R$^6$CO—NH—R$^7$OH      (III)

wherein $R^6$ is a linear or branched, saturated or unsaturated hydrocarbon group having 7 to 20 carbon atoms, $R^7$ is an ethylene group or a propylene group, $$R^4\text{—}O\text{—}(R^5O)_n\text{—}SO_3M \qquad (II)$$

wherein $R^4$ is a linear or branched, saturated or unsaturated hydrocarbon group having 8 to 20 carbon atoms, $R^5$ is an ethylene group or a propylene group, M is an alkali metal, an alkaline-earth metal, an ammonium ion, or a hydroxyalkyl-substituted ammonium having 2 or 3 carbon atoms, and n is the of from 0 to 8, which means an average number of moles, wherein the fatty acid monoalkylolamide is contained in an amount of from 3 to 10% by weight of the pearly luster composition and the alkyl sulfate is contained in an amount of from 5 to 1.5% by weight of the pearly luster composition.

18. A pearly luster composition comprising:

i) at least one fatty acid glycol ester represented by the formula (I):

$$Y\text{—}O\text{—}(CH_2CH_2O)_m\text{—}COR^3 \qquad (I)$$

wherein $R^3$ is a pentadecyl group or a heptadecyl group, Y is —$COR^3$ ($R^3$ is as defined above), and m is 1, meaning an average number of moles added, wherein the fatty acid glycol ester is contained in an amount of from 15 to 30% by weight of the pearly luster composition, ii) a polyoxyalkylene alkyl ether nonionic surfactant represented by the formula (C):

$$R^1\text{—}O\text{—}(R^2O)_p\text{—}H \qquad (C)$$

wherein $R^1$ is a linear or branched, saturated or unsaturated hydrocarbon group having 8 to 20 carbon atoms, $R^2$ is an ethylene group or a propylene group, and p is the number of from 1 to 12, meaning an average number of moles added, and iii) water, the pearly luster composition further comprising a saturated or unsaturated fatty acid having 14 to 18 carbon atoms, wherein the fatty acid as a crystallization additive is contained in an amount of from 0.3 to 3% by weight of the pearly luster composition and is contained in an amount of from 1.5 to 15 parts by weight based on 100 parts by weight of the fatty acid glycol ester.

\* \* \* \* \*